United States Patent [19]

Sakuragawa

[11] Patent Number: 6,117,676
[45] Date of Patent: Sep. 12, 2000

[54] TRANSFECTED HUMAN AMNIOTIC CELLS AND METHOD FOR PRODUCING A GENE PRODUCT

[75] Inventor: Norio Sakuragawa, Kodaira, Japan

[73] Assignee: Srl, Inc., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/641,214

[22] Filed: Apr. 30, 1996

[30] Foreign Application Priority Data

Jul. 27, 1995 [JP] Japan ..................................... 7-211193

[51] Int. Cl.⁷ .................................................... C12N 15/63
[52] U.S. Cl. ............................................ 435/366; 435/375
[58] Field of Search .............................. 435/320.1, 240.2, 435/6, 69.1, 172.3, 366, 375; 424/93.21; 935/62, 52, 32, 71, 65

[56] References Cited

PUBLICATIONS

Orkin et al. "Report and Recommendations of the Panel to Assess the NIH Investment in Research on Gene Therapy," NIH Report, Dec. 7, 1995.

Maurer et al. "The Use of Gamma–Interferon to Increase HLA Antigen Exrpession on Cultured Amniotic Cells Used for the Prenatal Diagnosis of 21–Hydroxylase Deficiency," Annals of the New York Academy of Sciences, vol. 458: 148–155, 1985.

Maurer et al. "Gamma Interferon Induces Dedtectable Serological and Functional Expression of DR and DP but not DQ antigens on cultured amniotic fluid cells," Tissue Antigens, vol. 31: 174–182, 1987.

Raniero et al. "Trans–Activation of Herpes Simplex Virus Type–1 Immediate Early Genes is Specifically Inhibited by Human Recombinant Interferons," vol. 159(2): 439–444, Mar. 15, 1996.

Mahieu et al. "Construction of a Ribozyme Directed against Human Interleukin–6 mRNA Evaluation of Its Catalytic Activity In Vitro and In Vivo," Blood, vol. 84(11): 3758–3765, Dec. 1, 1994.

Grunhaus et al. "Adenovirus as cloning vectors," Seminars in Virology, vol. 3: 237–252, 1992.

*Primary Examiner*—Karen M. Hauda

[57] ABSTRACT

The present invention provides a human amniotic cell in which a gene desired to be expressed is introduced, and wherein said human amniotic cell expresses the product encoded by said gene. The present invention also provides a method for treating hereditary diseases comprising transplanting the human amniotic cells.

2 Claims, 3 Drawing Sheets

TRANSFECTED HUMAN AMNIOTIC CELLS AND METHOD FOR PRODUCING A GENE PRODUCT

BACKGROUND OF THE INVENTION

I. Field of the Invention

The present invention relates to a transfected human amniotic cell and to a method for treating hereditary diseases using the same.

II. Description of the Related Art

Main conventional methods for gene therapy in which a foreign gene is introduced into a patient so as to treat a hereditary disease include a method utilizing cells as a drug delivery system (DDS). An example of gene therapy of this type is a method for treating a hereditary disease such as adenosine deaminase deficiency or purine nucleotide phosphorylase deficiency, in which the gene of such an enzyme is inserted into a retrovirus vector, bone marrow cells collected from a patient are transfected with the recombinant vector, and the transfected bone marrow cells are autogenously transplanted to the patient. With this method, since bone marrow cells of the patient are used and the transfected cells must be transplanted into the bone marrow, the damage to the patient is large. It is also known to introduce a foreign gene into lymphocytes of the patient and to give the lymphocytes back to the patient. However, with this method, the therapy must be repeatedly performed and hereditary diseases which can be cured by this method are limited.

On the other hand, since amniotic cells do not express HLA-A, B, C and DR antigens as well as $\beta_2$-microglobulin, and produce large amounts of lysosomal enzymes, the possibility to treat lysosomal storage diseases which are hereditary diseases using amniotic cells has been suggested (Adinolfi, M. et al., *Nature* 295:325–327, 1982). Thus, it is known to use amniotic cells as a DDS in therapies of hereditary diseases. Transplantation of amniotic tissue has been carried out for treating inborn errors of metabolism such as mucopolysaccharidosis and lipidosis, and the effectiveness of the therapies for a part of the patients has been confirmed (Tylki-Szymanska A et al., J. Inher *Metab Dis* 8:101–104, 1985; Sakuragawa N et al., *Brain & Dev* 14:7–11, 1992). Clinically, rejection reactions in these patients have not been reported. However, this technique utilizes the amniotic cells as a DDS of an enzyme which is intrinsically produced by the amniotic cells. It has not been suggested to introduce a foreign gene into amniotic cells, and actually transfected amniotic cells have not been reported. In addition, immunogenecity of the amniotic cells has not been studied in detail after the above-mentioned report.

SUMMARY OF THE INVENTION

An increase in the number of kinds of cells which can be used as a DDS in gene therapy is advantageous since the number of hereditary diseases which can be cured by gene therapy also increases. If a rejection reaction is not caused even when the cells are transplanted to other persons, it is not necessary to prepare the cells to be transplanted from the patient, thus the damage to the patient is decreased. In addition, since preliminarily prepared cells can be used for the therapy, gene therapy can be carried out promptly and effectively. Accordingly, an object of the present invention is to provide a novel transfected cell which can be used as a DDS in gene therapy, which is different from the conventionally known bone marrow cells and lymphocytes, which does not substantially cause a rejection reaction even if it is transplanted to other persons.

The present inventor intensively studied to discover that amniotic cells do not express HLA-class II antigen which play the most important role in rejection reactions in transplantation. The present inventor also discovered that amniotic cells and express HLA-class I antigen only slightly. Further, the present inventor succeeded in introducing a foreign gene into amniotic cells for the first time, thereby completing the present invention.

That is, the present invention provides a human amniotic cell in which a gene desired to be expressed is introduced, and which expresses the product encoded by said gene. The present invention also provides a method for treating hereditary diseases comprising transplanting human amniotic cells in which a normal gene is introduced and which express the product encoded by said gene, into a patient suffering from a hereditary disease in which the product of said gene is deficient, insufficient or abnormal.

By the present invention, a novel transfected cell which is useful for gene therapy was provided. By the present invention, it was discovered that human amniotic cells can be used as a DDS for gene therapy aiming at expression of a foreign gene, a purpose for which amniotic cells have not been used. Thus, the types of hereditary diseases which can be cured are increased. Further, since it is thought that the cell according to the present invention does not cause rejection reactions or topical inflammation even if it is transplanted to other persons, the cell can be transplanted to other persons. Therefore, it is not necessary to prepare the cells to be transplanted from the patient, and tissue-cultured cells can be used, so that the damage to the patient is small. Further, since preliminarily prepared transfected cells can be used, the therapy can be carried out promptly and effectively. Thus, it is expected that the present invention will contribute much to gene therapy.

BRIEF DESCRIPTION OF THE INVENTION

DETAILED DESCRIPTION OF PREFERRED EMBODIMENTS

Figure 1:
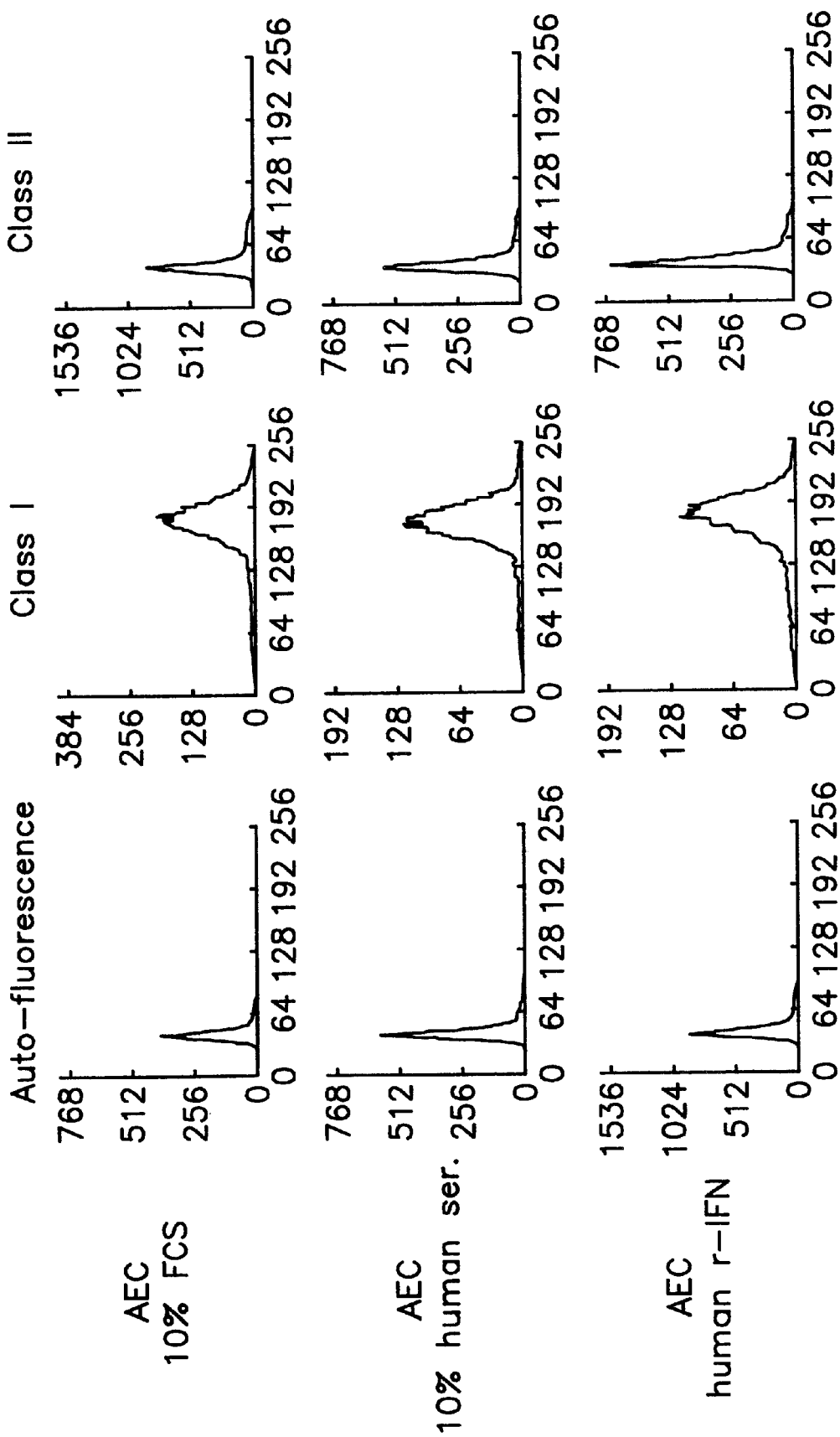
FIG. 1 shows flow cytometry profiles of the cells according to the present invention or the cells according to the present invention which were treated with γ-interferon, stained with anti-class I antigen or with anti-class II antigen.

As will be concretely described in the Reference Example below, the present inventor discovered that HLA-class II antigen does not exist at all on the surface of human amniotic cells, and the amount of HLA-class I antigen is very small. HLA-class II antigen is the most important immunogen in rejection reaction in transplantation. The fact that this antigen makes the use of the cells not expressed at all is very advantageous as a graft. This suggests that even an amniotic tissue from another person can be transplanted.

In addition, it is well-known that in various types of cells including monocytes, fibroblasts and endothelial cells, expression of class I and class II antigens is induced by γ-interferon. Since γ-interferon is produced by T lymphocytes, it is possible that class I and class II antigens are induced by the T cells that invade into the transplantation site, thereby causing topical inflammation. Thus, as described in the Reference Example below, human amniotic cells were cultured in the presence of γ-interferon to discover that neither class I nor class II antigen is induced at all on the surfaces of amniotic cells by γ-interferon. Therefore, it is thought that topical inflammation does not occur even if human amniotic cells are transplanted.

As described above, since human amniotic cells express no HLA-class II antigen which is most important in rejection reaction in transplantation, since expression of class I antigen is slight, and since these antigens are not induced by γ-interferon, the human amniotic cell is ideally suited to be transplanted. It is also thought that the cell can be transplanted into another person.

The human amniotic cell according to the present invention is one into which a gene desired to be expressed is introduced, and which expresses the product encoded by the gene. As will be described concretely in the Examples below, it was discovered that human amniotic cell can be transfected using vectors originated from SV40 or adenovirus. Vectors originated from retrovirus may also preferably be employed. Since these vectors are commercially available (or available from others), the transfected cell according to the present invention can be obtained by inserting a desired gene into the multicloning site of the vector, transfecting the human amniotic cells with the obtained recombinant vector, and selecting a clone producing the desired gene product. As the vector, vectors originated from adenovirus are especially preferred. As described in Example 2 below, by using an adenovirus vector, a surprising result that the transfection efficiency for cultured human amniotic cells was as high as about 100%. Transfection can be carried out by, for example, the conventional electroporation method using a commercially available electroporation apparatus.

The transfected cell according to the present invention can be used as a DDS for gene therapy. That is, to treat a hereditary disease in which the product of the gene is deficient, insufficient or abnormal, the human amniotic cells transfected with the above-mentioned vector in which the normal gene is inserted are transplanted to a patient. By so doing, the gene product produced by the transplanted transfected human amniotic cells is supplied to the body of the patient, so that the hereditary disease is cured or lightened. The hereditary diseases which may be cured by the cells for gene therapy according to the present invention are all hereditary diseases which may be cured by expression of a foreign gene. Preferred examples of the hereditary diseases which may be treated by the cells according to the present invention include Lesch-Nyhan syndrome, prolidase deficiency, glycogen storage disease and the like.

The gene therapy using the cells for gene therapy according to the present invention may be carried out by subcutaneously transplanting the cells. Although the site in which the cells are transplanted is not restricted, the cells may preferably be transplanted into abdominal sarcolemma, abdominal subcutis, or into brain tissues such as brain striate body. The number of cells to be transplanted is appropriately determined depending on the conditions of the patient and on the ability to produce the desired gene product of the cells according to the present invention. Usually, the number of the cells transplanted is about $10^5$ to $10^{10}$. The cells may be encapsulated with a plastic film having holes through which the desired gene product passes and the plastic film enclosing the cells may be embedded in the subcutis (*Experimental Neurology* 113, 322–329 (1991)).

EXAMPLES

The present invention will now be described by way of examples thereof. It should be noted that the examples are presented for the illustration purpose only and should not be interpreted in any restrictive way.

Reference Example: Preparation of Human Amniotic Cells and Characterization Thereof An amniotic epithelial layer was prepared by a known method (Akle et al., *Lancet II:* 1003–1005, 1981) from a placenta obtained from caesarean section. The separated amniotic sheet was dissected into several pieces and then treated with trypsin-EDTA (trypsin concentration: 0.1%) for 15 minutes. The isolated cells were collected by centrifugation, and then cultured in RPMI-1640 medium supplemented with 10% fetal calf serum under an atmosphere of 5% $CO_2$ in air at 37° C. Eighty $cm^2$ tissue culture flasks and near confluent cells were used for experiments.

The following mouse monoclonal antibodies were used: anti-human HLA class I antigen monoclonal antibody (DAKO A/S, Denmark, clone W6/32) and anti-human HLA-DR class II antigen, α-chain monoclonal antibody (DAKO, clone TAL.1B5). Also horse radish peroxidase (HRPO)-labeled goat F(ab')$_2$ anti-mouse Ig's (G+L) antibody (TAGO, INC. CA, USA) was used for the enzyme-labeled antibody method. For flow cytometry, monoclonal anti-human HLA class I antigen (as mentioned above) and monoclonal anti-human HLA-DR (DAKO, clone CR3/43) were used for detection of class I and II antigens as well as fluorescein conjugated anti-mouse immunoglobulin F(ab)$_2$ fraction (Silenus Lab. Hawthorn Victoria, Australia).

For flow cytometry, near confluent human amniotic cells from 80 $cm^2$ tissue culture flasks were harvested by treatment with trypsin-EDTA and then washed with cold PBS. The cells were subsequently incubated at 4° C. with the primary antibodies for 30 minutes and then resuspended with the FITC-conjugated second antibodies for 30 minutes at 4° C. The cells were then analyzed immediately with a flow cytometer (FCM-1D-JASCO Co., Tokyo).

To rule out the effects of γ-interferon on the induction of class I and class II antigens, the human amniotic cells prepared as described above were treated with γ-interferon (100 U/ml medium with 10% human serum of blood type AB, Sigma, USA) at 37° C. for 3 days. The resulting cells were analyzed by flow cytometry as described above.

The results of the flow cytometry are shown in FIG. 1. In FIG. 1, the abscissa indicates fluorescence intensity and the ordinate indicates the number of cells. FIG. 1B shows the results of the cells cultured in 10% human serum for 3 days. As shown in FIG. 1A, the cultured amniotic cells did not express the class II antigen at all on their surfaces as judged on comparison with the histogram for these cells stained with nonspecific mouse IgG1. Judging from its lower fluorescence intensity than that of lymphocytes as controls (not shown), the class I antigen was expressed slightly. Also, it was proved that the γ-interferon treatment neither increased the class I expression nor induced class II antigens (FIG. 1C)

On the other hand, a preparation of amniotic epithelial cells was incubated with either anti-class I primary antibody or anti-class II primary antibody at 37° C. for 1 hour. The cells were then incubated with a HRPO-conjugated antibody at 37° C. for 1 hour, followed by reacting the resultant with diaminobenzidine for 5 minutes at room temperature to generate color. As a result, the cells were not stained at all when the anti-class II monoclonal antibody was used and slightly stained when the anti-class I monoclonal antibody was used.

Example 1
Transfection of Human Amniotic Cells Using SV40 Vector

Figure 2:
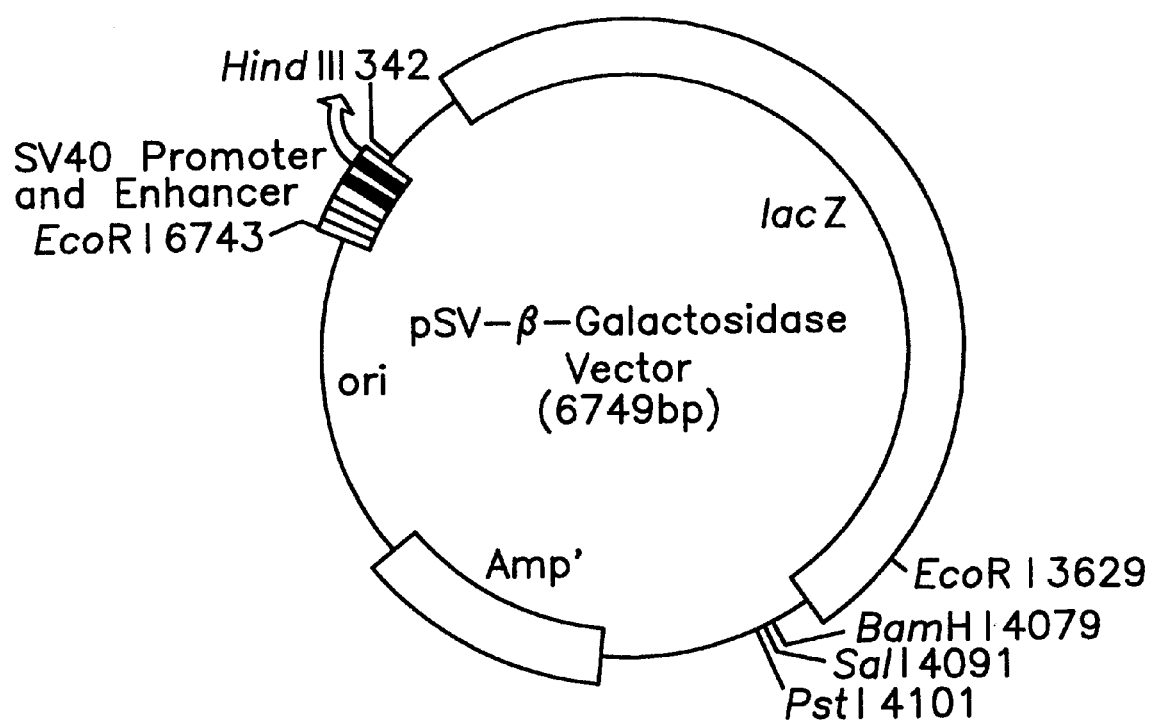
FIG. 2 is a gene map of pSV-β-galactosidase vector which is the recombinant vector used for transfection of human amniotic cells.

A pSV-β-galactosidase vector (Promega Corp., WI, USA), containing the β-galactosidase structural gene (lacZ) and the promoter and enhancer of SV40 was prepared by the modified cleared-lysate method (Sakuragawa et al., Cell Transplantation 4: 343–346, 1995). The gene map of pSV-β-galactosidase vector is shown in FIG. 2. Twenty μg of pSV-β-galactosidase was transfected into 4×10$^6$ amniotic cells by means of electroporation using an electroporation apparatus (GENE PULSER, Bio Rad Lab., CA, USA) and inoculated into 60 mm dishes. After growth for 48 hours at 37° C., the cells were fixed and evaluated by staining with 5-bromo-4-chloro-3-indoyl-β,D-galactoside (X-gal). As a result, 2 or 3 cells per a 60 mm dish had β-galactosidase activity. Thus, it was proved that human amniotic cells can be transfected with a SV40 vector.

Example 2
Transfection of Human Amniotic Cells Using Adenovirus Vector

Figure 3:
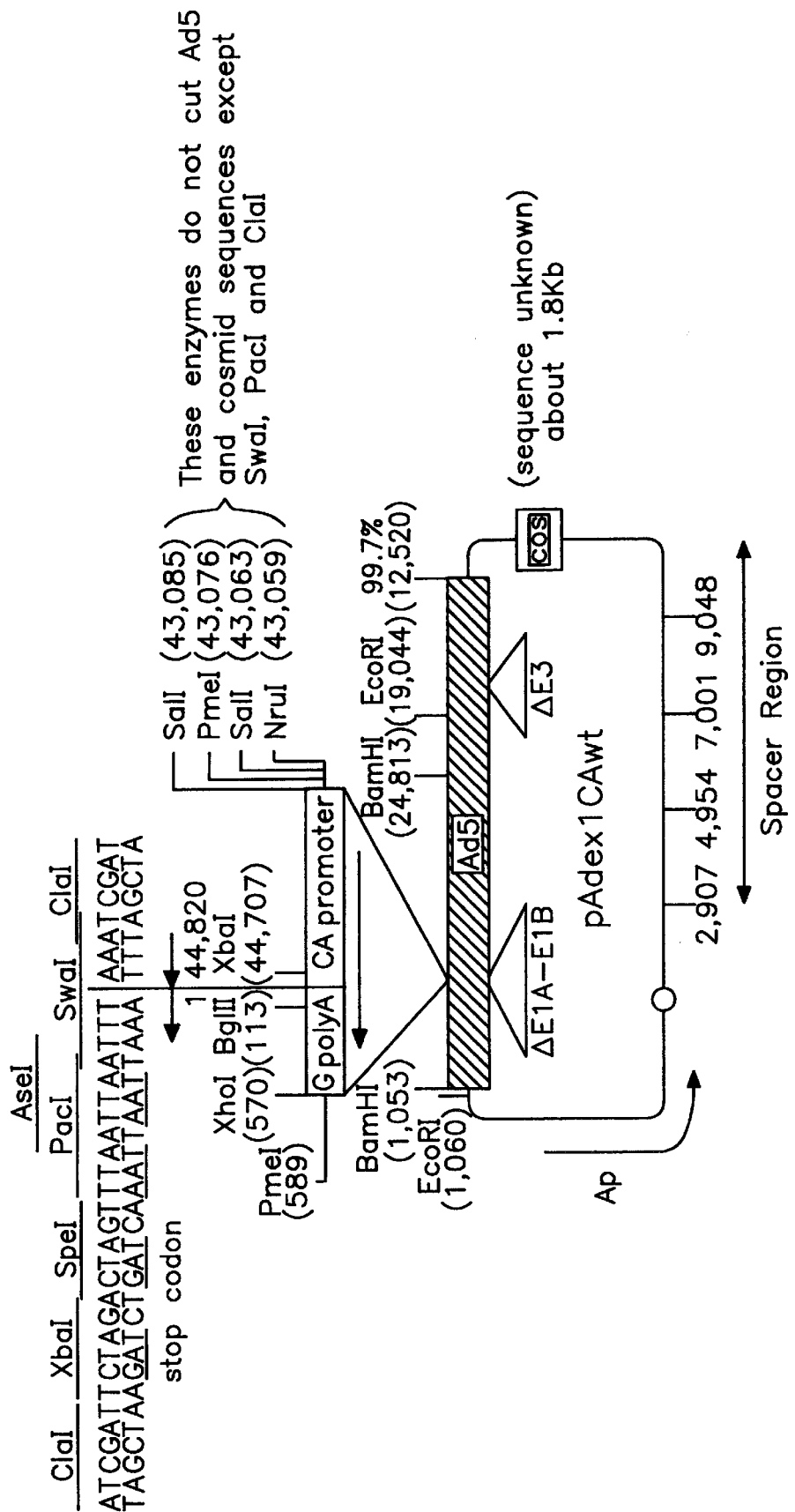
FIG. 3 is a gene map of pADEX1CA-LACZ which is the recombinant vector used for transfection of human amniotic cells (SEQ ID NO: 1 and SEQ ID NO: 2 are shown).

Into the multicloning site of an adenovirus vector pADEXlCA ("JIKKEN IGAKU", Vol. 12, No. 15 (extra edition), 1994, pp.34–39, available from Dr. Izumi SAITO, Gene Analysis Center, Medical Science Laboratories, Tokyo University), lacZ gene was inserted to obtain pADEXlCA-LACZ (this recombinant vector was given by Dr. Izumi SAITO, Gene Analysis Center, Medical Science Laboratories, Tokyo University). A gene map of this recombinant vector is shown in FIG. 3. Human amniotic cells were transfected with this recombinant vector at a moi of 20 and expression of lacZ was examined using X-gal. As a result, substantially 100% of the cells expressed lacZ. By this, it was proved that human amniotic cells are transfected by an adenovirus vector with a surprisingly high efficiency.

Example 3
Transplantation of Transfected Human Amniotic Cells

10$^6$ human amniotic cells prepared in Example 2, into which lacZ gene was introduced, were transplanted into rat brain striate body stereoencephalotomically. One week later, the rat was sacrificed and a perfusion-fixed sample of the transplanted region was prepared by a conventional method. The sample was immunohistochemically analyzed. That is, to identify the lacZ gene, the sample was stained with X-gal. As a result, cells stained with blue were observed at the transplanted region in the brain.

Since existence of live cells stained in blue was confirmed, it was proved that gene therapy may be carried out by transplantation of the cells of the present invention.

What is claimed is:

1. An in vitro method for transfecting human amniotic cells comprising, transfecting said human amniotic cells with a recombinant adenovirus encoding a desired gene, wherein the gene is expressed by said human amniotic cells.

2. The method of claim 1, wherein said human amniotic cells have been obtained from the epithelial layer of a human placenta.

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: adenovirus vector

<400> SEQUENCE: 1
atcgattcta gactagttta attaatttaa atcgat         36

<210> SEQ ID NO 2
<211> LENGTH: 36
<212> TYPE: DNA
<213> ORGANISM: adenovirus vector

<400> SEQUENCE: 2
tagctaagat ctgatcaaat taattaaatt tagcta         36